United States Patent
Heid et al.

(10) Patent No.: US 7,417,433 B2
(45) Date of Patent: Aug. 26, 2008

(54) METHOD, EXAMINATION APPARATUS AND ANTENNA ARRAY FOR MAGNETIC RESONANCE DATA ACQUISITION

(75) Inventors: Oliver Heid, Gunzenhausen (DE); Markus Vester, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 90 days.

(21) Appl. No.: 11/436,211

(22) Filed: May 17, 2006

(65) Prior Publication Data
US 2007/0013376 A1 Jan. 18, 2007

(30) Foreign Application Priority Data
May 17, 2005 (DE) .................. 10 2005 022 551

(51) Int. Cl.
*G01V 3/00* (2006.01)
(52) U.S. Cl. ...................... 324/318; 600/421
(58) Field of Classification Search ............. 324/322, 324/311, 300, 318; 600/421
See application file for complete search history.

(56) References Cited

U.S. PATENT DOCUMENTS

| 5,245,288 | A   | 9/1993  | Leussler |
| 6,791,322 | B2  | 9/2004  | Vester |
| 6,906,520 | B2  | 6/2005  | Heid et al. |
| 7,123,009 | B1* | 10/2006 | Scott ................... 324/311 |
| 7,230,425 | B2* | 6/2007  | Leussler ............... 324/318 |

* cited by examiner

*Primary Examiner*—Louis M Arana
(74) *Attorney, Agent, or Firm*—Schiff Hardin LLP (57) ABSTRACT

In a method for implementation of a magnetic resonance examination, and a magnetic resonance apparatus, and an array for acquisition of magnetic resonance signals, and a magnetic resonance signal at a magnetic resonance frequency are acquired from an examination region with an array of frequency conversion units after an RF excitation and are radiated as frequency-converted signals. The resulting signal field is acquired by a number of reception antennas of a second antenna array, which are arranged at different spatial positions and thus allow a spatial resolution of the frequency-converted signals. The acquired acquisition signals are used for image reconstruction.

45 Claims, 7 Drawing Sheets

METHOD, EXAMINATION APPARATUS AND ANTENNA ARRAY FOR MAGNETIC RESONANCE DATA ACQUISITION

BACKGROUND OF THE INVENTION

1. Field of the Invention

The present invention concerns a method for implementation of a magnetic resonance examination (MR examination) with an MR apparatus, of the type wherein MR signals with an MR frequency are acquired from an examination region with an antenna array after a radio-frequency excitation (RF excitation). The invention furthermore concerns a magnetic resonance apparatus and an antenna array for acquisition of magnetic resonance signals.

2. Description of the Prior Art

MR examinations enable spatially-resolved imaging of an examination region. For reasons of the achievable signal-to-noise ratio, in MR apparatuses it is advantageous to use local or surface coils for acquisition of MR signals from only a limited small region of the subject. Such coils are normally connected with an evaluation device via cables. The cables and the necessary plug contacts represent a limitation to the user-friendliness and the reliability of the surface coil and the corresponding signal transmission. It is known to transfer magnetic resonance signals from the coil arrangement to the evaluation unit via an optical cable.

It is also known to convert an acquired magnetic resonance signal into another frequency and to wirelessly transmit it to the evaluation device. Such a linear frequency conversion with transistor or diode mixers is known, for example, from DE 41 26 537 A1. The receiver for the frequency-converted signal is located only a few meters from the site of the evaluation unit. If an array of coils that supply MR signals independently of one another is used for the acquisition of MR signals from different body segments, these MR signals are then converted into different frequencies. In the frequency conversion, the MR signal is mixed with a mixer signal having a constant frequency in a mixing stage.

Furthermore, a linear frequency conversion with parametric amplification is known from DE 102 19 749 A1. In the transmission method based thereupon, an MR signal is acquired by an MR reception antenna at an MR frequency and is supplied to a non-linear reactance. Auxiliary (supplementary) energy is supplied by an auxiliary antenna with at least one auxiliary frequency. One part of the auxiliary energy is acquired by the auxiliary reception antenna and supplied with the auxiliary frequency to the non-linear reactance and there is mixed together with the MR signal to form a mix signal with a mix frequency. The mix signal is supplied to a mix signal transmission antenna and is emitted thereby. It is subsequently acquired by a mix signal reception antenna and supplied to the evaluation device.

When an additive signal at an additive frequency, that is equal to the difference of the auxiliary frequency and the magnetic resonance frequency is generated by the non-linear reactance and the additive signal is supplied to an absorption circuit resonant at the additive frequency, a higher radiated energy results at the mix frequency. The absorption circuit is connected in parallel with, for example, the non-linear reactance. The energy emitted by the mix signal transmission antenna becomes greater the further that the auxiliary frequency deviates from the MR frequency. Such an energy supply enables a locally-acquired MR signal to be wirelessly transmitted to a control and evaluation device in a simple manner. A transfer of MR signals that are acquired by a number of coils of an array is also possible with the method according to DE 102 19 749 A1. For this purpose, the auxiliary frequencies and the mix frequencies resulting from the auxiliary frequencies and the MR signals are selected such that the individual auxiliary and mix signal frequencies do not mutually influence one another. It is thereby even possible to emit an auxiliary signal via a single broadband auxiliary transmission antenna, with the auxiliary signal containing a number of auxiliary frequencies that differ from one another. The auxiliary signal can be acquired by a single broadband auxiliary reception antenna and be supplied to the mixer arrangements via input filter circuits.

A transmission method for an analog magnetic resonance signal by means of frequency modulation is known from DE 101 48 462 C1. Method for digital transmission with time, frequency or code multiplexing are known from telecommunications.

SUMMARY OF THE INVENTION

An object of the present invention is to simplify the operation of a magnetic resonance apparatus with an antenna array formed by a number of antenna elements.

The above object is achieved in accordance with the invention by a method wherein, in an embodiment, the acquired MR signals are acquired by antenna elements of a first antenna array, converted by frequency converters into a common frequency band and radiated from the antenna elements as frequency-converted signals. The spatial pattern of-the MR reception field strength in the first antenna array is translated into a pattern similar to the strength of the signal field formed by the radiated and the frequency-converted signals. A number of reception antennas of a second antenna array acquire acquisition signals in this frequency band. These acquisition signals are used for image reconstruction. An advantage of the invention is that the spatial resolution upon reception of the MR signals by the use of the array of frequency converter units is maintained by the second antenna array since the short wavelength of the, for example, microwave frequency (for example $\lambda/2=5$ cm) of the frequency band of the frequency-converted signals is limited by diffraction, and not by the long wavelengths of the MR frequency (for example $\lambda/2=2.4$ m). For this purpose, the second antenna array can be arranged, for example, at the tube wall surrounding the examination region. The field pattern of the signal field on the second antenna array is thus linked (in a manner that can be reversed without losses in the signal-to-noise ratio) with the field pattern of the MR signals at the frequency conversion units. For example, in comparison to the prior art the method according to the invention avoids the elaborate generation of many different phase-locked auxiliary carriers as well as many highly-selective filters at a large number of different frequencies. In comparison to the frequency-modulated transmission of MR signals, the power requirement is smaller and the required total bandwidth is significantly less.

In another embodiment, the frequency conversion ensues by means of an auxiliary radiation at an auxiliary frequency that lies in the microwave range, and is radiated onto the first antenna array and acquired thereby. To reduce the interference, the auxiliary radiation can be radiated at a phase-modulated and/or frequency-modulated auxiliary frequency, with the modulation in the signals being cancelled by analog or digital means.

A circularly-polarized auxiliary radiation has the advantage of making the transmission insensitive to relative rotations of the antenna elements.

In a preferred embodiment of the method, the acquired MR signals with the auxiliary radiation are linearly converted in the frequency converters into frequency-converted signals that differ from the auxiliary frequency by the MR frequency.

In a further embodiment of the method, the antenna elements radiate the frequency-converted signals such that a signal field results in the frequency band that is acquired by the reception antennas of the second antenna array, with the reception antennas being arranged surrounding the examination region.

It is advantageous for the frequency converter to radiate the auxiliary radiation to the first antenna array as homogeneously as possible. The phase and/or amplitude distributions of the auxiliary radiation can be activated such that the radiation of the first antenna array ensues uniformly. Alternatively, by controlling the phase and/or amplitude distributions, it is possible to introduce a spatially-dependent phase and/or amplitude into the frequency conversions in order to associate spatial Fourier components of the MR signal with the -reception antennas of the second antenna array through a lens-like formation of the converted signals.

To avoid losses of the subsequent radio transmission, it is advantageous to provide a moderate signal amplification (for example 10 dB). Either the MR signal and/or the frequency-converted signal can be amplified in the frequency conversion units. The energy supply of the frequency conversion, in particular of the mixer and/or of the amplification, ensues from the auxiliary radiation.

In another embodiment of the method, in the MR imaging the acquisition signals of the second antenna array are used to calculate the currents in each of the antenna elements by, for example, the surfaces of the first antenna arrays being used that have matching phase factors and the linear combination of the signals arising therefrom being inverted given the propagation of the frequency-converted signal. The image reconstruction then ensues in the typical manner given the usage of coil-specific transferred MR signals. This explicit inversion, however, is not absolutely necessary for many typical MR imaging techniques (MR phased array, SENSE, SMASH), since these implement a self-calibration of the MR sensitivity pattern anyway. In such cases, the acquisition signals of the second antenna array can proceed directly into the image reconstruction.

In summary, for the method antennas are required to, (1) acquire the MR signals, (2) emit the frequency-converted signals, (3) possibly acquire an auxiliary radiation and (4) acquire the frequency-converted signal field. The antennas with regard to (1) and (2) (and possibly also (3)) can be fashioned as one antenna. The frequency-conversion units thus embody antennas for the points (1) through (3) in addition to the frequency converters.

The above object also is achieved in accordance with the invention by a magnetic resonance apparatus having a transmission unit for radiation of an auxiliary signal with an auxiliary frequency. The transmission unit can be a modulation for phase and/or frequency modulation of the auxiliary frequency and/or a distributor for phase and/or amplitude distribution to the array of frequency-conversion units.

In one embodiment of the apparatus, the frequency converter has a passive mixer (for example a resistive diode mixer) or an active mixer (in particular with an intrinsic amplifier), for example a transistor mixer or a parametric reactance mixer.

The receivers at the second antenna array can be coupled in a phase-locked manner for the acquisition of frequency-converted signals, in particular via a synchronization line. This makes the processing of the reception signals of the reception antennas easier.

For inverse mixing (reconversion) of the second antenna array, in one embodiment the magnetic resonance apparatus can have at least one inverse frequency mixer that mixes one of the reception signals back into the magnetic resonance frequency band by means of the auxiliary frequency, and is connected with one of the outputs of the second antenna array for an image reconstruction in the MR frequency band.

The above object also is achieved in accordance with the invention by an array for acquisition of MR signals in MR examinations having reception units for spatially-resolved acquisition of MR signals triggered by an RF excitation in an examination region of an MR apparatus (which MR signals are triggered in an MR frequency band) and at least two frequency converters. The frequency converters are designed for generation of a frequency-converted signal field from the MR signals in a frequency-converted frequency band, in particular with an equal frequency. The signal field contains information about the location of the-acquisition of the magnetic resonance signals. An advantage of such an array is that it converts the spatial structure of the MR signal field into a frequency-converted signal field similar in terms of its structure to the original MR field. The spatial information of the field of the MR signals is retained in the transmission and can be wirelessly transmitted from the examination region to an imaging unit essentially without signal-to-noise losses.

DESCRIPTION OF THE PREFERRED EMBODIMENTS

Figure 1:
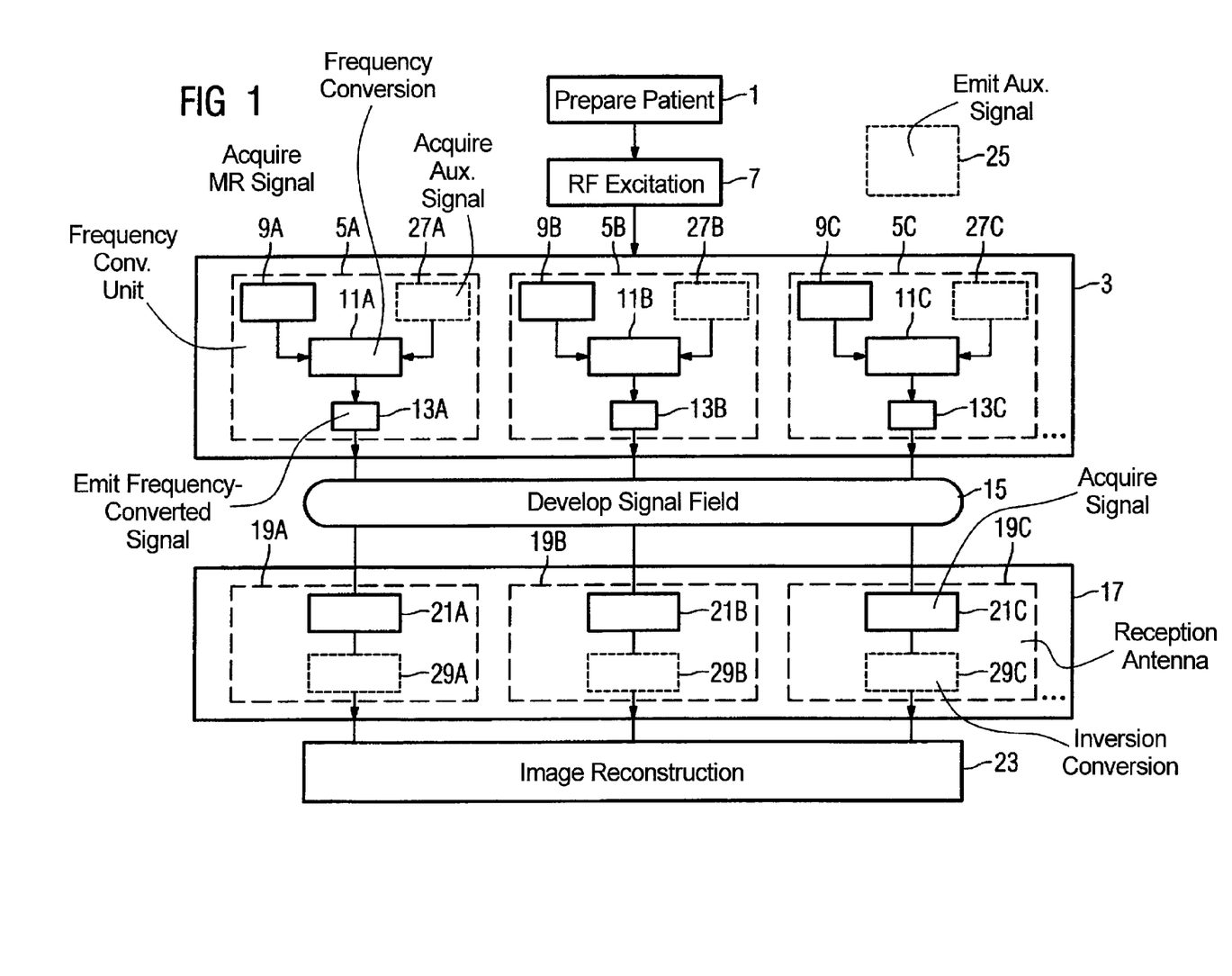
FIG. 1 is a flowchart for explanation of the wireless transfer of MR signals in accordance with the invention.

In an exemplary flowchart, FIG. 1 illustrates an embodiment of the method for implementation of an MR examination with an MR apparatus in accordance with the invention. In step 1, a patient is prepared for MR examination, meaning that the patient is positioned on a patient bed of the MR apparatus and an array 3 of frequency conversion units 5A, 5B, 5C, . . . to be used is arranged corresponding to a region of the patient to be examined. The frequency conversion units 5A, . . . serve for the acquisition of spatially resolved MR signals. If the preparation is concluded, the patient is inserted into the examination region of the MR apparatus, meaning the region to be examined is positioned in the isocenter of the basic magnetic field for the MR examination. The RF excitation 7 that excites the MR signals in the examination region now ensues. For the acquisition steps 9A, 9B, 9C ... of the MR signals, the frequency conversion units 5A, ... are, for example, arranged in a laminar manner next to one another and each includes an MR reception antenna. Frequency conversion steps 11A, 11B, 11C ... ensue in the respective frequency conversion units 5A, .... In each frequency conversion step 11A, ... the MR signal is converted into a frequency-converted signal which, for example, lies in the microwave-frequency range. With a corresponding antenna that, for example, can also be the antenna for MR reception, the frequency-converted signals are now emitted (transmission steps 13A, 13B 13C ... ) by each of the frequency conversion units 5A, .... Development 15 of a signal field in the frequency-converted frequency band thereby occurs. Acquisition signals are acquired (acquisition steps 21A, 21B, 21C ... ) in the frequency-converted frequency band with a further antenna arrangement 17 with a number of reception antennas 19A, 19B, 19C .... The acquisition signals are the starting point of an image reconstruction 23.

The frequency conversion can ensue using auxiliary radiation at an auxiliary frequency. This is indicated in FIG. 1 by the steps of emission of an auxiliary signal and the acquisition thereof in acquisition steps 27A, 27B, 27C ... by the auxiliary radiation in the individual antenna elements 5A, ... The emission of the auxiliary radiation at the auxiliary frequency can ensue, for example, with a transmission antenna independent of the second antenna array 17 or using the reception antennas 19A, ....

The image reconstruction 23 can ensue either directly in the frequency-converted frequency band or even with the use of an inverse conversion of the acquisition signals in steps 29A, 29B, 29C ... by the reception antennas 19A in the MR frequency band. For example, the auxiliary frequency can be used again to convert the acquisition signal back into the MR frequency band.

Figure 2:
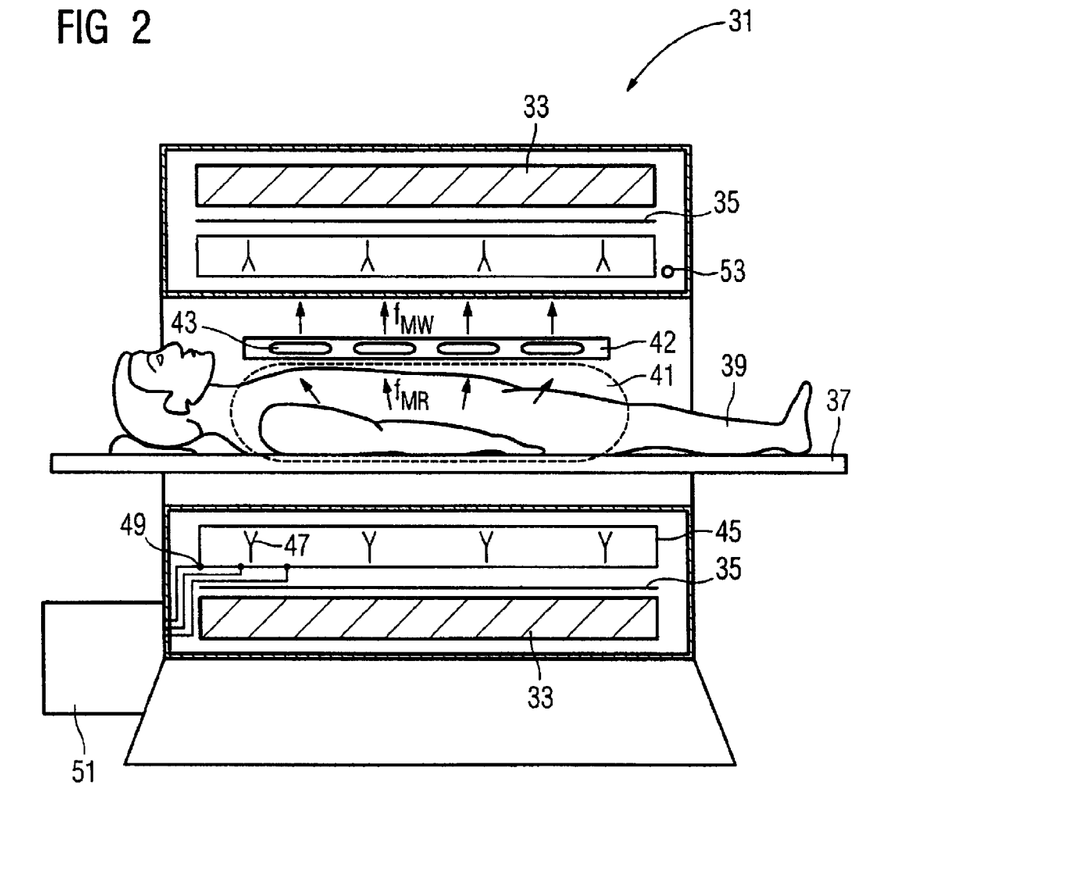
FIG. 2 is a sectional view of an MR apparatus in accordance with the invention.

FIG. 2 shows a sectional view of an MR apparatus 31 with a basic field magnet 33, an RF antenna 35 and a patient bed 37 on which a patient 39 has been positioned and inserted into the examination region 41 of the MR apparatus 31. One or more antenna arrays 42 with multiple frequency conversion units 43 for the acquisition of the MR signals are arranged on the patient 39.

MR signals in the frequency-range $f_{MR}$ are emitted by the body of the patient after excitation, and are detected in the frequency conversion units 43. The detected MR signals are converted in terms of their frequency and, for example, emitted as microwave signals in the frequency range $f_{MW}$. A signal field thereby arises between the array 42 of frequency conversion units 43 and a second antenna array 45. The second antenna array 45 has a number of reception antennas 47 that, for example, are arranged surrounding the patient 39 or the examination region 41; for example, behind the tube-shaped inner cladding in the case of a hollow-cylindrical MR apparatus or on plate-shaped cladding parts above or, respectively, below the patient in the case of an open MR apparatus. Outputs 49 of the second antenna array 45 are connected with an imaging unit 51 of the MR apparatus 31. The image reconstruction occurs there either in the MR frequency band after inverse conversion, or in the frequency-converted frequency band.

The frequency conversion can ensue with an additional transmission unit 53 which radiates an auxiliary radiation with an auxiliary frequency onto the array 42 of frequency conversion units 43. Alternatively, the auxiliary radiation can be emitted with the second antenna array 45.

Figure 3:
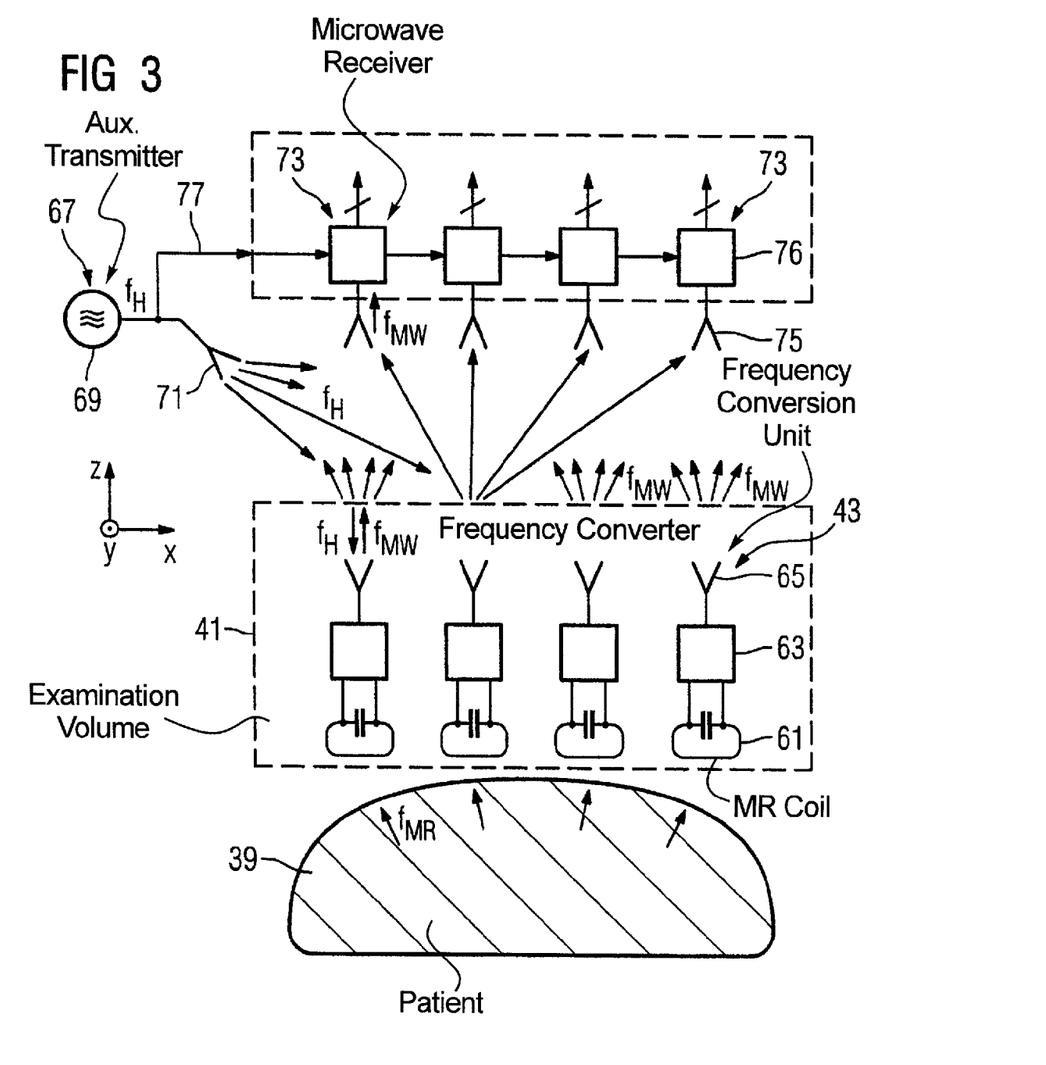
FIG. 3 schematically illustrates wireless transmission from a first antenna array to a second antenna array in accordance with the invention.

FIG. 3 explains an inventive design using an auxiliary radiation. The patient 39 is the source of the magnetic resonance signals with the frequency $f_{MR}$. The frequency conversion units 43 are formed by MR coils 61, frequency converters 63 and microwave transmission antennas 65. Using, for example, dipole or patch antennas, the frequency conversion units 43 enable the conversion of the magnetic resonance field into, in this case, a microwave signal field that is used for wireless signal transmission.

The frequency conversion ensues with an auxiliary frequency $f_H$ that is emitted by an auxiliary transmitter 67, which includes a frequency generator 69 and a microwave transmission antenna 71. The frequency conversion units 43 thus are homogeneously irradiated. The microwave transmission antennas 65 serve both for acquisition of the auxiliary signal and for emission of the microwave signals. The microwave signals propagate from the antenna elements to the tube wall (surrounding the patient) of the magnetic resonance apparatus. Located there are corresponding microwave receivers 73 with microwave reception antennas 75 that acquire the microwave field and forward it to the reception units 76 for acquisition of the magnetic resonance data. The microwave receivers 73 are coupled with one another in a phase-locked manner, for example with the auxiliary transmitter 67 via a synchronization line 77.

Figure 5:
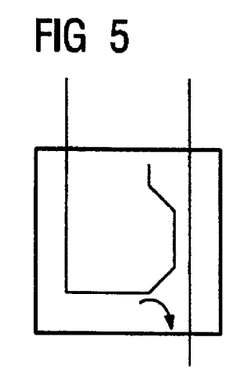
FIGS. 5 through 8 show different variants for switches (duplexers) in the second antenna array in accordance with the invention.
Figure 6:
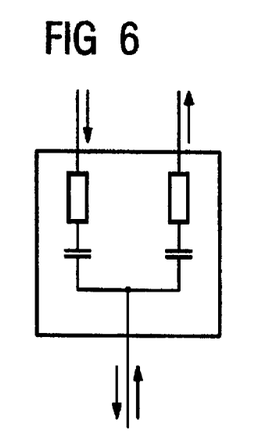
Figure 7:
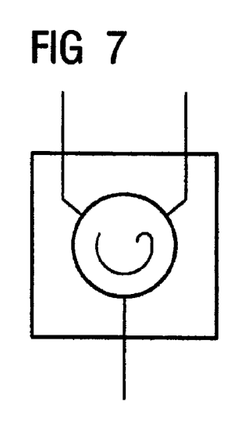
Figure 8:
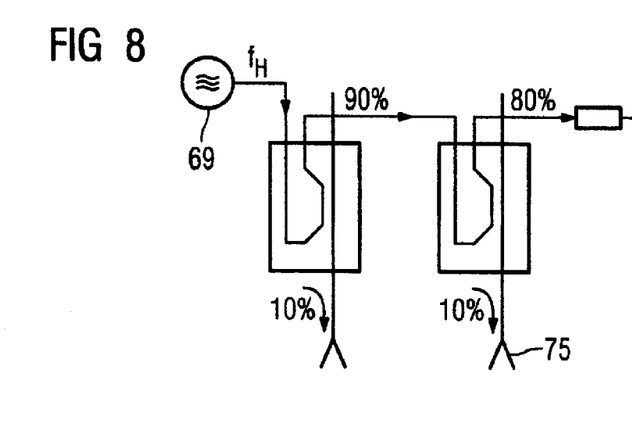

The microwave antennas 75 can be used both for the emission of the auxiliary frequency and for the acquisition of the frequency-converted MR signals. One possible design with regard to this is explained in FIG. 4. The feed of the auxiliary frequency thereby ensues via switches 79. For emission of the auxiliary frequency, at least one of the microwave reception antennas 75 is used as a transmission antenna and is thereby connected with a distributor 81 via a switch 79. The distributor 81 supplies the auxiliary frequency from the frequency generator 69 to the microwave antenna or the various microwave antennas 75. A directional coupler (FIG. 5), a selective diplexer with a filter (FIG. 6) or a circulator (FIG. 7) could be used as a switch. The static measurement field necessary for operation of the circulator could be the basic magnetic field of the basic field magnet 33 of the MR apparatus 31. The supply of the microwave reception antennas with the auxiliary frequency alternatively can ensue using a series of cascaded directional couplers according to FIG. 8. In this embodiment, each microwave reception antenna 75 is supplied, for example, with 10% of the transmission signal.

Figure 4:
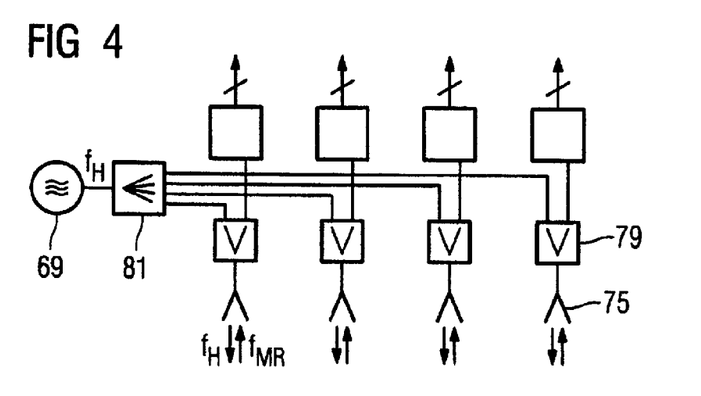
FIG. 4 explains the use of an auxiliary radiation in accordance with the invention.

The auxiliary radiation preferably is radiated uniformly onto the entire surface of the first antenna array and correspondingly be homogeneously provided to the various frequency converters. The uniformity of the acquired auxiliary frequency signals can be optimized or an intentional spatially-dependent phase can be introduced into the frequency conversion by control of the phase and amplitude distributions. For this purpose, for example, phase modulators and/or amplitude modulators can be inserted between the distributor 81 ad the switch 79. For example, a lens-like formation of the acquisition signals can be achieved by means of a quadratic auxiliary carrier phase at the frequency converters, the quadratic auxiliary carrier phase being dependent on location, such that an approximate association of the microwave reception antennas with the spatial Fourier components of the MR acquisition signal is possible.

A spatial transfer function of the 2D field pattern between a parallel plane of the array of frequency conversion units ($z=0$) and the tube wall ($z=h$) is outlined in the following.

A pattern of the MR acquisition signals (Fourier representation in the plane of the frequency conversion units (z=0)) can be described via the following equation:

$$b_{MR}(x,y,t,z=0) = \text{Integral}(B_{MR}(k_x,k_y)\exp(-j(k_x x + k_y y + \omega_{MR} t))) dk_x dk_y$$

The field pattern of the MR transmission antennas that is emitted with the amplification V, assumes the following form:

$$b_{MW}(x,y,t,z=0) = V\, b_{MR}(x,y,t)^* \exp(-j\omega_H t)$$

$$V\, \text{Integral}(B_{MR}(k_x,k_y)\exp(-j(k_x x + k_y y + \omega_{MW} t))) dk_x dk_y$$

At the site of the tube wall (plane z=h), an acquired MW field pattern results:

$$B_{MW}(k_x,k_y,z=h) = B_{MW}(k_x,k_y,z=0)\exp(-jh(k_0^2 - k_x^2 - k_y^2)^{0.5})$$

with $k_0 = \omega_{MW}/c$

The propagation factor $\exp(-jh(k_0^2 - k_x^2 - k_y^2)^{0.5})$ is thereby a pure phase factor for $k_x^2 + k_y^2 < k_0^2$ energy loss up to the diffraction limit) or a damping factor for $k_x^2 + k_y^2 > k_0^2$ (exponential decrease of the fields with increasing distance).

For example, in the method an auxiliary frequency of 3 GHz is distributed and radiated over a wide area via the direction couplers. Each frequency conversion unit acquires the auxiliary frequency at 3 GHz with a microwave antenna. With a parametric amplifier as a linear frequency converter, each of the frequency conversion units converts the magnetic resonance signal from 63 . . . 65 MHz to 3.063 . . . 3.065 GHz. The frequency conversion units transmit this mixed product again via the microwave antennas, such that the microwave antennas of the second antenna array on the tube wall can acquire signals in this frequency range and can forward them to receivers for 3.064 GHz.

Figure 9:
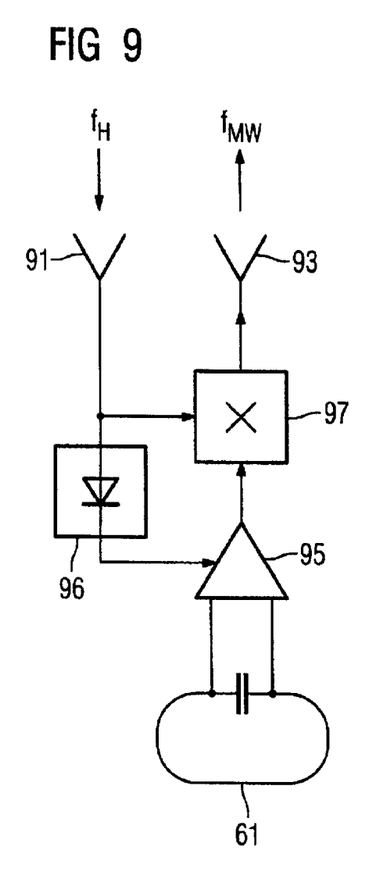
FIGS. 9 and 10 show examples for a frequency converter with an amplifier and s passive mixer in accordance with the invention.
Figure 10:
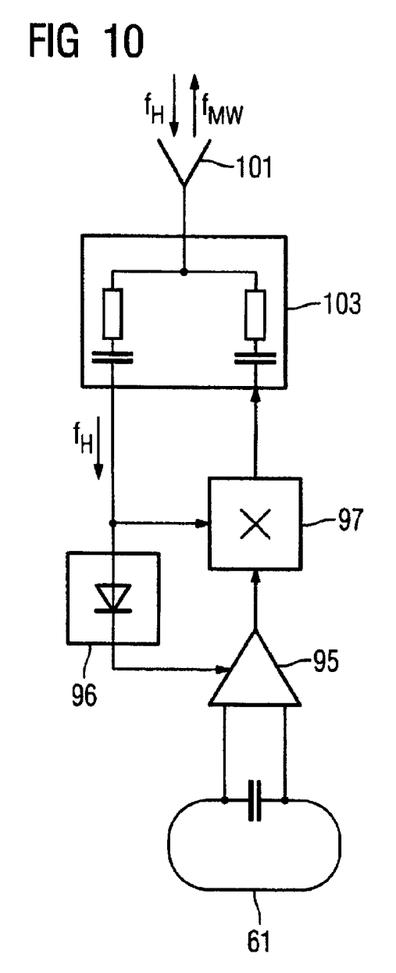

FIGS. 9 and 10 are examples for frequency conversion units with amplifiers and a passive mixer. A first microwave reception antenna 91 and a microwave transmission antenna 93 are recognized in FIG. 9. The MR signal acquired with the MR coil 61 is supplied to an MR preamplifier 95. This is supplied with energy via a rectifier 96 with the aid of the auxiliary frequency acquired by the microwave reception antenna 91. The acquired auxiliary frequency $f_H$ is supplied to a mixer 97 together with the MR signal. Its output is connected with the microwave transmission antenna 93 for emission of the frequency-converted signal.

A common microwave antenna 101 for acquisition of the auxiliary frequency $f_H$ and for emission of the microwave frequency $f_{MW}$ is used in FIG. 10. For this, in comparison with FIG. 9 a diplexer 103 is connected between the common antenna 101 and the mixer 97 or the rectifier 96.

Figure 11:
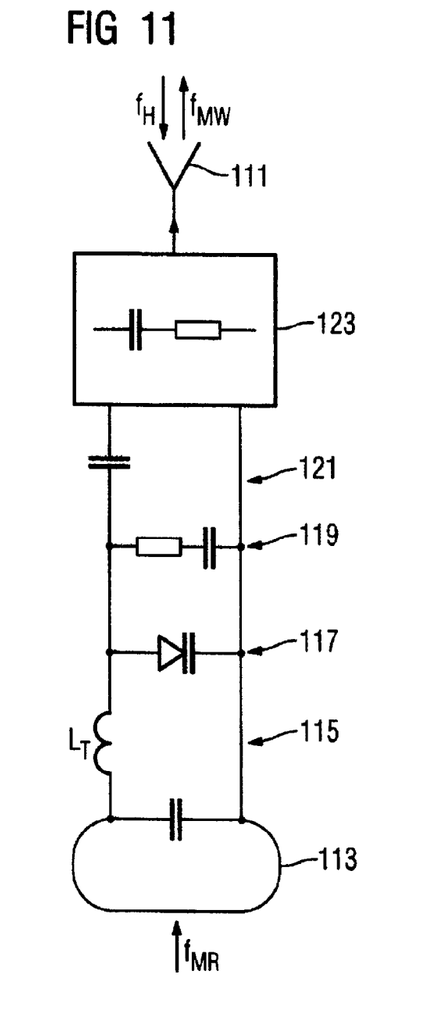
FIGS. 11 and 12 show examples for frequency converters with a parametric amplifier in accordance with the invention.
Figure 12:
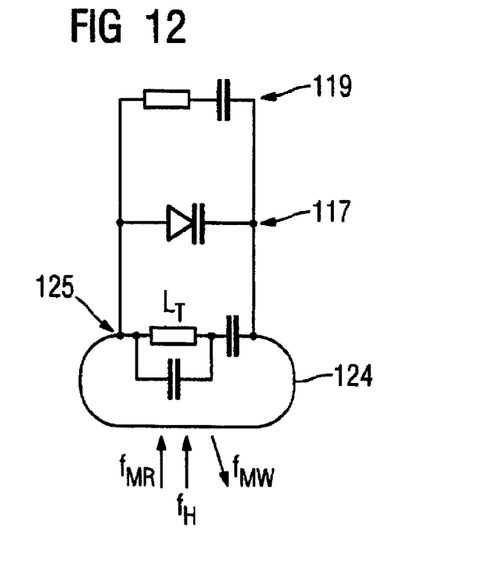

FIGS. 11 and 12 show examples for frequency conversion with parametric amplifiers. In FIG. 11, a microwave antenna 111 serves for acquisition of the auxiliary frequency $f_H$ and for the emission of the frequency-converted signal with $f_{MW}$. The magnetic resonance signal is detected by an MR antenna 113 and connected with a varactor 117, with an absorption circuit with the frequency $f_S$ and with a high-pass 121 via a low-pass 115 and with the microwave antenna 111 via a microwave adaptation circuit 123.

In comparison with FIG. 11, a further simplification with regard to the number of the antennas has been effected in FIG. 12, in which the microwave and magnetic resonance examination antennas are merged into a common oscillation circuit 124. A low-pass 125 is additionally introduced for this.

Figure 13:
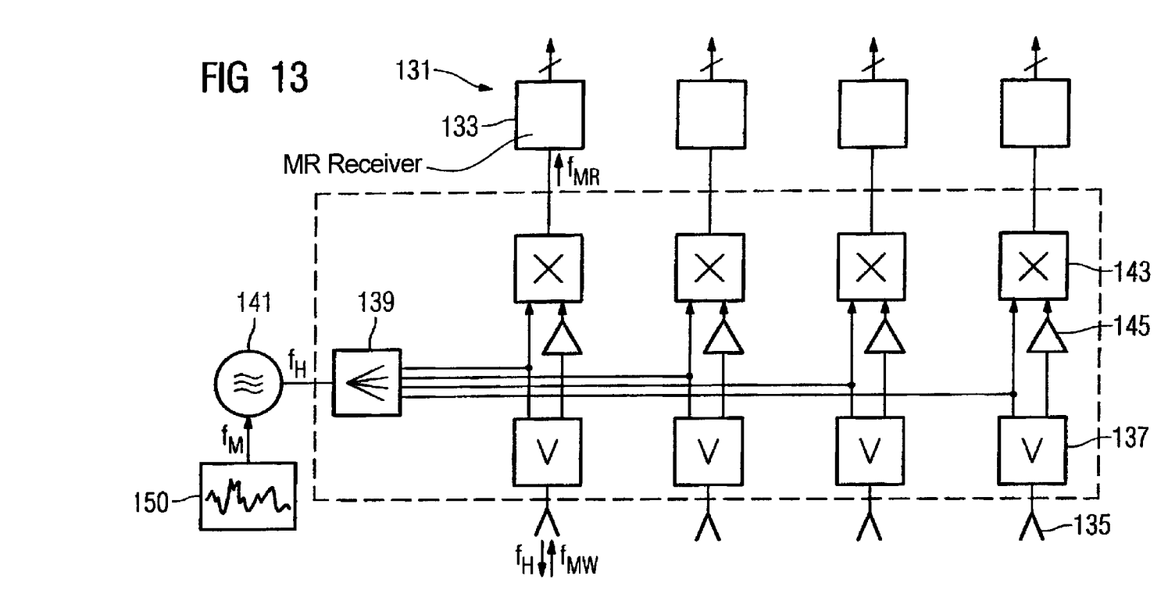
FIG. 13 illustrates inverse conversion of the reception signals in the MR frequency band with cancelling of the auxiliary frequency in accordance with the invention.

FIG. 13 illustrates the principle of the inverse mixing of acquisition signals in the MR frequency band. The inverse mixing has the advantage that the processing is phase-independent and, on the receiver side, a typical standard MR acquisition technology 131 with standard MR receivers 133 can be used. In the example, the microwave antennas 135 are again connected via switches 137 with a distribution 139 and the auxiliary frequency generator 141 on the one hand. This transmission-side connection between switch 137 and distributor 139 is additionally connected with a mixer 143 that mixes the acquisition signal which passes through the switch 137 as well as a microwave preamplifier 145 back into the MR frequency range again with the aid of the auxiliary frequency $f_H$. The output of the mixer 143 is connected with the input of the MR receiver 133.

Figure 14:
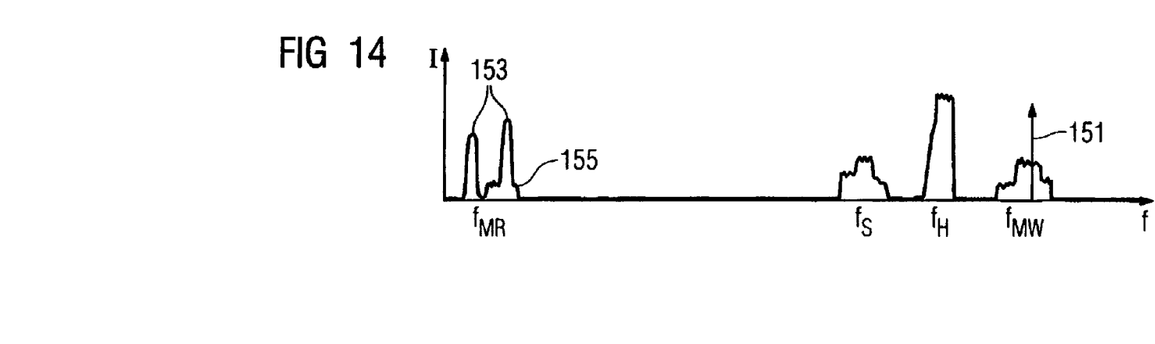
FIG. 14 shows a spectrum with cancelling of the auxiliary signals.

To reduce the interference, the auxiliary signal or, respectively, the auxiliary frequency $f_H$ is spectrally blurred with a pseudo-random sequence generator 150. The sensitivity with regard to a source of interference (noise) 151 is correspondingly reduced. This can be seen, for example, in the frequencies in the spectrum with blurring corresponding to FIG. 14. MR signals 153 are plotted, and the source of interference 151 in the microwave range given the wireless transmission leads to a blurred baseline in the transmitted and inversely-mixed MR signal 155. Furthermore, the auxiliary frequency $f_H$, the somewhat lower frequency of the absorption circuit focal spot and the frequency-converted frequency $f_{MW}$ with the source of interference 151 are detected in the spectrum.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for acquiring magnetic resonance data with a magnetic resonance examination apparatus, comprising the steps of:
    exciting nuclear spins in an examination region of a subject by irradiating the subject with RF energy, thereby causing emission of magnetic resonance signals from the examination region;
    with an array of frequency conversion units, receiving said magnetic resonance signals and converting said magnetic resonance signals into frequency-converted signals in a common frequency band;
    radiating said frequency-converted signals to generate a signal field that contains location information identifying a location of acquisition of the magnetic resonance signals;
    spatially positioning a plurality of reception antennas in an antenna array for spatially-resolved acquisition of said signal field, each reception antenna generating an acquisition signal that contains said location information; and
    computationally reconstructing an image of said examination region from said acquisition signals received by said plurality of reception antennas in said antenna array.

2. A method as claimed in claim 1 wherein the step of converting said magnetic resonance signals into frequency-converted signals in a common frequency band comprises converting said magnetic resonance signals into frequency-converted signals each having the same frequency.

3. A method as claimed in claim 1 comprising forming each of said frequency conversion units from an antenna element connected to a frequency converter, with the respective antenna elements of said frequency conversion units, in combination, forming an additional antenna array.

4. A method as claimed in claim 3 wherein the step of radiating said frequency-converted signals comprises radiating said frequency-converted signals from said additional antenna array to generate said signal field.

5. A method as claimed in claim 3 comprising radiating auxiliary radiation at an auxiliary frequency onto said additional antenna array, and using said auxiliary radiation in said frequency conversion units to generate said frequency-converted signals.

6. A method as claimed in claim 5 comprising radiating said auxiliary radiation at an auxiliary frequency in the microwave range.

7. A method as claimed in claim 5 wherein the step of converting said magnetic resonance signals into frequency-converted signals in a common frequency band comprises linearly converting said magnetic resonance signals into said frequency-converted signals with said auxiliary radiation to produce frequency-converted signals differing in frequency from said auxiliary frequency by the magnetic resonance frequency.

8. A method as claimed in claim 5 comprising radiating said auxiliary radiation from an independent transmission antenna.

9. A method as claimed in claim 5 comprising radiating said auxiliary radiation from said antenna array.

10. A method as claimed in claim 9 comprising feeding said auxiliary radiation into said antenna array through at least one feed element selected from the group consisting of directional couplers, selective diplexers with filters, and circulators.

11. A method as claimed in claim 5 comprising uniformly radiating said auxiliary radiation onto said frequency conversion units.

12. A method as claimed in claim 11 comprising radiating said auxiliary radiation onto the respective antennas of said additional antenna array with a uniformity distribution among the respective antennas selected from the group consisting of phase distribution and amplitude distribution.

13. A method as claimed in claim 12 comprising controlling said uniformity distribution to introduce a spatially-dependent factor, selected from the group consisting of spatially-dependent phase and spatially-dependent amplitude, into the frequency conversion to associate spatial Fourier components of the magnetic resonance signals with the respective reception antennas of said antenna array.

14. A method as claimed in claim 5 comprising generating a detuning signal to detune the antenna elements of said additional array during excitation with said RF energy, by modulating said auxiliary frequency.

15. A method as claimed in claim 5 comprising radiating said auxiliary radiation as circularly polarized auxiliary radiation.

16. A method as claimed in claim 5 comprising generating a detuning signal to detune the antenna elements of said additional array during excitation with said RF energy, by modulating said auxiliary frequency.

17. A method as claimed in claim 5 comprising radiating said auxiliary radiation with a modulation selected from the group consisting of frequency modulation and phase modulation, to reduce interference, and subsequently cancelling said modulation in said acquisition signals.

18. A method as claimed in claim 3 comprising forming one of said frequency converters by a passive mixer connected to an amplifier.

19. A method as claimed in claim 3 comprising forming one of said frequency from an active mixer with an intrinsic amplifier.

20. A method as claimed in claim 1 comprising spatially distributing said reception antennas of said antenna array to surround the examination region.

21. A method as claimed in claim 1 wherein the step of frequency converting said magnetic resonance signal includes amplifying at least one of said magnetic resonance signal and said frequency-converted signal.

22. A method as claimed in claim 1 comprising phase-locked coupling the respective reception antennas of said antenna array.

23. A method as claimed in claim 1 comprising using only acquisition signals in said image reconstruction that are in said frequency band of said frequency-converted signals.

24. A method as claimed in claim 1 comprising reconstructing said image by mixing said acquisition signals back into a selected band of the magnetic resonance frequency.

25. A magnetic resonance examination apparatus comprising:
an RF transmitter that excites nuclear spins in an examination region of a subject by irradiating the subject with RF energy, thereby causing emission of magnetic resonance signals from the examination region;
an array of frequency conversion units that receive said magnetic resonance signals and converting said magnetic resonance signals into frequency-converted signals in a common frequency band;
a radiator that radiates said frequency-converted signals to generate a signal field that contains location information identifying a location of acquisition of the magnetic resonance signals;
a plurality of reception antennas in an antenna array for spatially-resolved acquisition of said signal field, each reception antenna generating an acquisition signal that contains said location information; and
an image reconstruction unit that computationally reconstructs an image of said examination region from said acquisition signals received by said plurality of reception antennas in said antenna array.

26. An apparatus as claimed in claim 25 wherein said array of frequency conversion unit converts said magnetic resonance signals into frequency-converted signals each having the same frequency.

27. An apparatus as claimed in claim 25 wherein each of said frequency conversion units comprises an antenna element connected to a frequency converter, with the respective antenna elements of said frequency conversion units, in combination, forming an additional antenna array.

28. An apparatus as claimed in claim 27 wherein said radiator is formed by said additional antenna array.

29. An apparatus as claimed in claim 27 comprising an auxiliary radiator that radiates auxiliary radiation at an auxiliary frequency onto said additional antenna array, and wherein said frequency conversion units additionally detect said auxiliary radiation.

30. An apparatus as claimed in claim 29 wherein said frequency-conversion units convert said magnetic resonance signals into frequency-converted signals in a common frequency band by linearly converting said magnetic resonance signals in frequency-converted signals with said auxiliary radiation to produce frequency-converted signals differing in frequency from said auxiliary frequency by the magnetic resonance frequency.

31. An apparatus as claimed in claim 29 wherein said auxiliary radiator is formed by said antenna array, and wherein said apparatus comprises at least one feed element that feeds said auxiliary radiation into said antenna array, selected from the group consisting of directional couplers, selective diplexers with filters, and circulators.

32. An apparatus as claimed in claim 29 wherein said auxiliary radiator radiates said auxiliary radiation with a modulation selected from the group consisting of frequency modulation and phase modulation, to reduce interference.

33. An apparatus as claimed in claim 32 wherein said auxiliary radiator radiates said auxiliary radiation onto the respective antennas of said additional antenna array with a uniformity distribution among the respective antennas selected from the group consisting of phase distribution and amplitude distribution.

34. An apparatus as claimed in claim 33 wherein said array of frequency-conversion units controls said uniformity distribution to introduce a spatially-dependent factor, selected from the group consisting of spatially-dependent phase and spatially-dependent amplitude, into the frequency conversion to associate spatial Fourier components of the magnetic resonance signals with the respective reception antennas of said antenna array.

35. An apparatus as claimed in claim 34 wherein one of said frequency converters comprises a passive mixer connected to an amplifier.

36. An apparatus as claimed in claim 27 wherein one of said frequency comprises an active mixer with an intrinsic amplifier.

37. An apparatus as claimed in claim 27 wherein said antenna array comprises at least one inverse frequency mixer that mixes said acquisition signals back into a selected band of the magnetic resonance frequency, using said auxiliary frequency.

38. An apparatus as claimed in claim 25 wherein the respective reception antennas of said antenna array are phase-locked coupled to one another.

39. An apparatus as claimed in claim 25 wherein said reception antennas of said antenna array are spatially distributed to surround the examination region.

40. An apparatus for acquisition of magnetic resonance signals in a magnetic resonance examination, comprising:

an antenna array comprised of a plurality of antenna elements that respectively acquires spatially-resolved magnetic resonance signals from an examination subject in a magnetic resonance frequency band, said magnetic resonance signals having been triggered by an RF excitation of the subject; and a plurality of frequency converters respectively connected to said plurality of antenna elements, each frequency converter generating a signal in a conversion frequency band from the magnetic resonance signal supplied thereto by the antenna element connected thereto, by frequency conversion of the magnetic resonance signals supplied thereto in the magnetic resonance frequency band, said signal in the conversion frequency band comprising information identifying a location in the subject from which the magnetic resonance signal in the magnetic resonance frequency band originated.

41. An apparatus as claimed in claim 40 wherein at least one of said frequency converters comprises an input for receiving the magnetic resonance signal from the antenna element connected thereto and an input supplied with an auxiliary signal having an auxiliary frequency that differs from the frequency of the frequency converted signal, and wherein said frequency converter mixes said magnetic resonance signals supplied thereto with the auxiliary signal supplied thereto.

42. An apparatus as claimed in claim 41 wherein said frequency converter comprises a passive mixer.

43. An apparatus as claimed in claim 41 wherein said frequency converter comprises a resistive diode mixer.

44. An apparatus as claimed in claim 43 wherein each frequency converter comprises an amplifier combined with said resistive diode mixer.

45. An apparatus as claimed in claim 40 wherein at least one of said frequency converters comprises an active mixer selected from the group consisting of transistor mixers and parametric reactance mixers.

* * * * *